United States Patent [19]
Mulier et al.

[11] Patent Number: 5,876,398
[45] Date of Patent: Mar. 2, 1999

[54] METHOD AND APPARATUS FOR R-F ABLATION

[75] Inventors: Peter M. J. Mulier, St. Paul; Michael F. Hoey, Shoreview, both of Minn.

[73] Assignee: Medtronic, Inc., Minneapolis, Minn.

[21] Appl. No.: 574,526

[22] Filed: Dec. 19, 1995

Related U.S. Application Data

[63] Continuation of Ser. No. 302,304, Sep. 8, 1994, abandoned.

[51] Int. Cl.$^6$ .................................................. A61B 17/36
[52] U.S. Cl. .............................. 606/41; 128/898; 606/45; 607/101
[58] Field of Search ........................ 606/41, 42, 45–50; 607/100–102, 115, 116, 119, 122, 127, 126

[56] References Cited

U.S. PATENT DOCUMENTS

| | | |
|---|---|---|
| 4,463,765 | 8/1984 | Gold .......................... 607/127 |
| 4,506,680 | 3/1985 | Stokes . |
| 4,940,064 | 7/1990 | Desai . |
| 5,030,204 | 7/1991 | Badger . |
| 5,060,660 | 10/1991 | Gambale . |
| 5,083,565 | 1/1992 | Parins . |
| 5,104,393 | 4/1992 | Isner . |
| 5,122,137 | 6/1992 | Lennox . |
| 5,165,421 | 11/1992 | Fleischaker . |
| 5,281,213 | 1/1994 | Milder . |
| 5,334,193 | 8/1994 | Nardella ....................... 606/41 |
| 5,336,222 | 8/1994 | Durgin, Jr. et al. ............ 606/50 |
| 5,348,554 | 9/1994 | Imran . |
| 5,403,311 | 4/1995 | Abele et al. ................... 606/49 |
| 5,431,649 | 7/1995 | Mulier et al. ................. 606/41 |
| 5,433,708 | 7/1995 | Nichols . |
| 5,500,012 | 3/1996 | Brucker et al. ............... 607/122 |
| 5,507,743 | 4/1996 | Edwards et al. ............... 606/41 |
| 5,507,802 | 4/1996 | Imran ........................... 607/122 |

FOREIGN PATENT DOCUMENTS

| | | |
|---|---|---|
| 591680 | 9/1993 | European Pat. Off. ........... 607/127 |
| 3516830 | 11/1986 | Germany . |
| 1544396 | 12/1987 | U.S.S.R. . |
| 1690786 | 6/1989 | U.S.S.R. . |
| 92/20401 | 11/1992 | WIPO ............................ 607/127 |

*Primary Examiner*—Michael Peffley
*Attorney, Agent, or Firm*—Reed A. Duthler; Harold R. Patton

[57] ABSTRACT

An ablation catheter particularly adapted for use in ablation of cardiac tissue. The catheter is provided with an elongated electrode, intended to make contact with tissue to be ablated, in the heart, along its length. The electrode is mounted to a segment of the catheter which is porous, and the catheter is provided with an internal lumen for delivery of a conductive fluid such as Ringer's solution, to the porous portion of the catheter body, so that the conductive solution may be delivered along the entire length of the electrode.

9 Claims, 2 Drawing Sheets

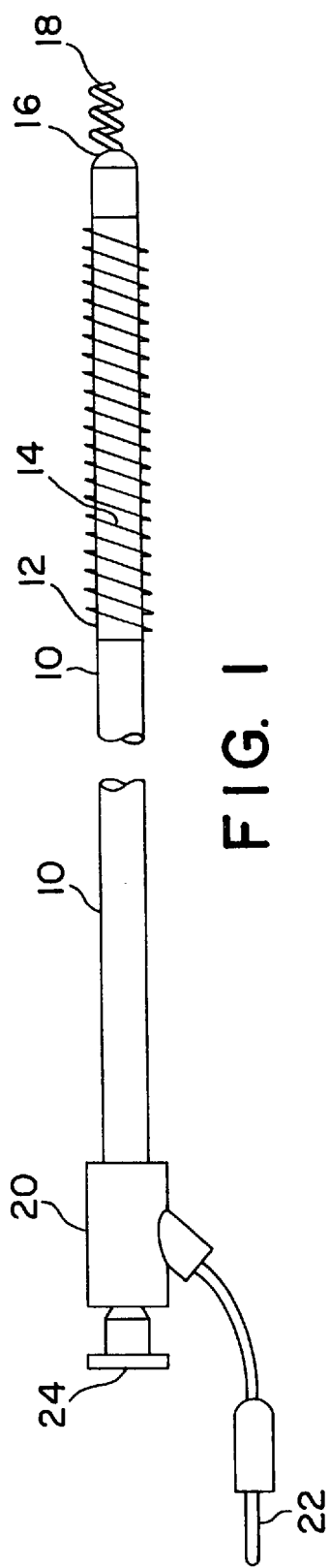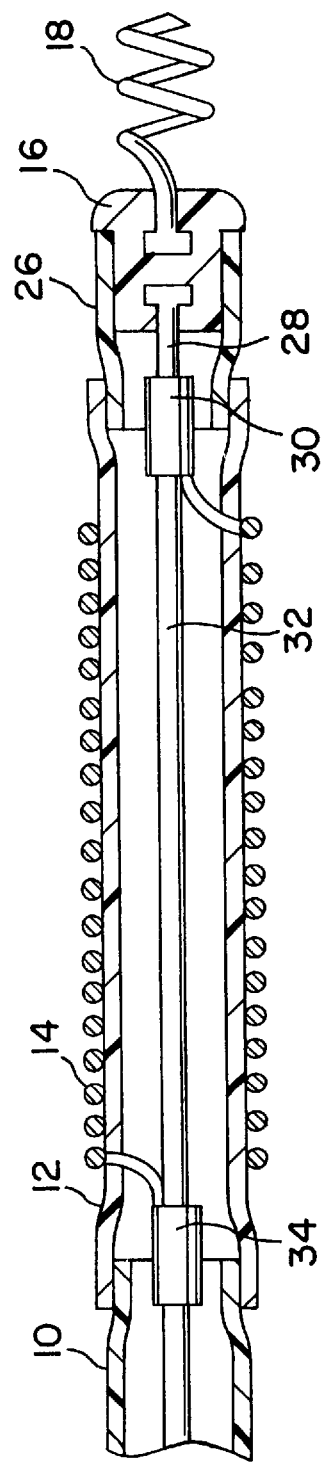

METHOD AND APPARATUS FOR R-F ABLATION

This is a continuation of application Ser. No. 08/302,304 filed on Sep. 8, 1998, now abandoned.

BACKGROUND OF THE INVENTION

This invention relates generally to the field of devices for cardiac surgery, and more specifically to devices for R-F ablation of cardiac tissue.

The present invention is directed toward treatment of tachyarrhytmias, which are heart rhythms in which an chamber or chamber of the heart exhibits an excessively fast rhythm. In particular, the present invention is directed toward treatment of tachycardias, which are due to the presence of ectopic foci within the cardiac tissue or due to the presence of aberrant condition pathways within the cardiac tissue.

Therapies have been developed for treating tachycardias by destroying cardiac tissue containing identified ectopic foci or aberrant conduction pathways. A variety of approaches have been taken, including application of electrical energy or other forms of energy to destroy the undesired cardiac tissue. As examples, ablation of cardiac tissue has been accomplished by means of radio frequency electrical current, microwave energy, heat, electrical pulses, cryothermy, and lasers. At present, ablation using R-F energy is perhaps the most widely practiced in the context of ablation procedures that can be carried out by means of a catheter, inserted into the closed heart.

Most R-F ablation catheters employ electrodes which are intended to contact the endocardium of the heart, or, as in U.S. Pat. No. 5,083,565, are intended to penetrate the endocardium and enter the myocardium. In general, R-F ablation catheters are effective to induce small lesions in heart tissue including the endocardium and inner layers of myocardium, in the immediate vicinity of the electrode. However, the medical community has expressed a desire for devices which produce larger lesions, to reduce the number of applications of R-F energy (burns) required to effectively ablate the cardiac tissue associated with the tachycardia.

R-F ablation causes tissue in contact with the electrode to heat through resistance of the tissue to the induced electrical current therethrough. The actual extent of heating is somewhat unpredictable. However, temperature tends to rise as the duration and amplitude of the R-F signal increase. Heating of the tissue beyond a certain point can cause dissection or charring of the tissue, resulting in a high impedance between the R-F electrode and the return electrode, which in turn leads to cessation of the heating process, and, in some cases, causes the electrode to stick to the charred tissue. One response to this phenomenon has been the inclusion of thermocouple within the ablation electrode, in conjunction with feedback control to modulate the R-F signal to maintain the electrode temperature at a set parameter. One such system is disclosed in U.S. Pat. No. 5,122,137.

SUMMARY OF THE INVENTION

The present invention is directed toward improving the consistency and efficacy of R-F ablation, by accurately determining the ablation site and by increasing the overall size and extent of the lesions induced by R-F ablation. These goals are pursued by means of an ablation catheter employing an elongated electrode extending of substantial length, e.g. 2–10 cm, located adjacent the distal end of the catheter and means for delivering a flow of conductive, cooling fluid along the length of the electrode.

In its disclosed embodiment, the electrode takes the form of an elongated conductive coil mounted around the distal portion of the catheter body, which is porous to allow flow of fluid out of the catheter, in the vicinity of the electrode coil. The catheter body is provided with a central lumen coupled at its proximal end to a fluid fitting, which allows delivery of physiologic Ringer's solution, saturated Ringer's solution, saline solution or other conductive or coolant liquids to the porous portion of the catheter body. The use of highly conductive fluids such as a saturated Ringer's solution is particularly desirable in conjunction with the present invention. In the disclosed embodiment, a helical screw is provided at the distal end of the catheter to allow for fixation of the tip of the catheter to heart tissue. The elongated electrode in conjunction with the delivered conductive fluid provide the capability of creating an elongated, linear lesion, which is believed preferable to and substantially easier to accomplish than a series of individual lesions.

BRIEF DESCRIPTION OF THE DRAWINGS

FIG. 1 is a plan view of a catheter adapted to perform the improved method of R-F ablation, according to the present invention.

FIG. 2 is a cutaway view through the distal end of the catheter illustrated in FIG. 1.

DETAILED DESCRIPTION OF THE PREFERRED EMBODIMENTS

Figure 3:
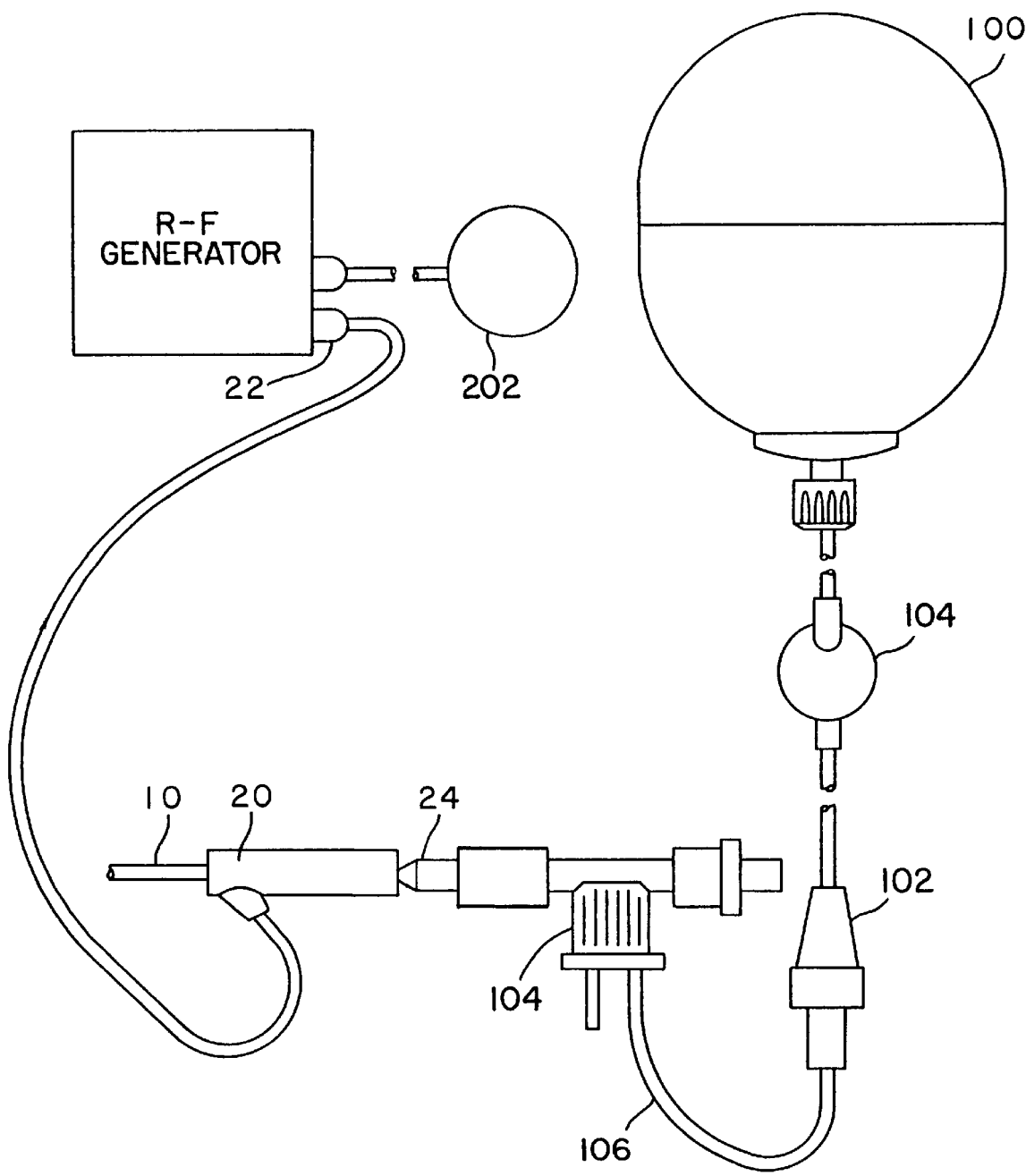
FIG. 3 is a plan view of a fluid delivery system adapted for use in conjunction with the present invention.

FIG. 1 is a plan view of a catheter according to the present invention. An elongated catheter body 10 is provided which carries a manifold 20 at its proximal end, carrying a fluid connector 24 and an electrical connector 22. At the distal end of the catheter, an elongated coiled electrode 14 is located over a porous segment 12 of the catheter body. Fluid fitting 24 is coupled via an internal lumen to the interior of the porous segment 12. Electrode 14 is coupled by an internal conductor to electrical connector 22. At the distal most end of the lead is located a helical screw 18, mounted to a plastic tip 16. Helical screw 18 is insulated from electrode 14, and is employed to locate the distal end of the catheter at a desired location.

In use, the catheter may be advanced to its desired located by passing the catheter through a guide catheter of fixed configuration or through a deflectable or deformable guide catheter, in order to locate the distal end of the catheter at a desired location within the heart. Alternatively, a deflectable stylet or guidewire may be inserted into the internal lumen and used to control the movement of the catheter through the vascular system. The screw 18 is screwed into the heart tissue, and the guide catheter or stylet is withdrawn while the ablation catheter is pressed forward in order to locate the helical electrode 14 along a desired line of tissue within the heart. Fluid fitting 24 is coupled to a source of fluid, such as Ringer's solution, which may be delivered by means of a pump to the porous section of electrode 12, and RF energy is applied to electrode 14, by means of electrical connector 22. The delivered Ringer's or other conductive solution serves both to more evenly distribute the current applied via electrode 14 and to cool the tissue adjacent electrode 14, preventing overheating and desiccation of the tissue.

FIG. 2 is a cutaway view through the distal tip of the catheter illustrated in FIG. 1. In this view, it can be seen that a torque cable 32, which may correspond to the torque cable illustrated in U.S. Pat. No. 5,165,421, incorporated herein by reference in its entirety, is coupled to the distal tip member 16 by means of pin 28 and fair rule 30 which is crimped to both the torque cable 32 and pin 28. Crimped ferrule 30 also couples the distal end of electrode coil 14 to the torque cable, while the proximal end of the coil electrode 14 is coupled to the torque cable by a second crimped ferrule 34. Torque cable 32 serves both to electrical couple electrical connector 22 (FIG. 1) to electrode 14 and to transmit torque along the length of the catheter, allowing screw 18 to be screwed into tissue.

Electrode 14 is mounted around a porous sleeve 12, which is in turn coupled to the distal end of outer catheter tube 10 and to the proximal end of catheter tube 26. Porous sleeve 12 may be fabricated of a porous material, such as porous PTFE, commercially sold as Goretex®, by W.L. Gore & Company. Alternatively, sleeve 12 could be fabricated of silicone rubber, polyurethane or other biocompatible plastic and provided with small formed apertures such as bores, slits or other fluid passageways, allowing for escape of fluid along the entire length of coil 14.

In the embodiment illustrated, helical screw 18 is electrically insulated from the remainder of the catheter. However, in some embodiments, it may be desirable to make helical screw 18 available as an ablation electrode, and it might therefore be coupled to torque cable 32, and electrode 14 coupled to a second conductor within the catheter body, extending proximally to a second electrical connector. In such an alternative embodiment, the torque cable may be provided with a central passageway, and the helical screw might be made hollow, allowing for delivery of the conductive fluid through the helical electrode, as disclosed in co-pending application Ser. No. 08/113,441 for a "Method and Apparatus for RF Ablation" filed on Aug. 27, 1993 by Mulier et al., incorporated herein by reference in its entirety.

FIG. 3 illustrates a pressurized source for Ringer's solution which may be employed to deliver Ringer's solution to the electrode of the catheter described above. A reservoir 100 is provided, which is commercially manufactured by Block Medical Inc., and sold under the brand name "Home Pump". The reservoir contains Ringer's solution and provides Ringer's solution at one atmosphere pressure to flow control 102, via filter 104. Flow control 102 may, for example, provide a flow limit of 20 drops or 1 cc per minute. Flow control 102 is coupled to a second flow control element 104, which, in the experimental apparatus employed by the inventors allows for additional adjustability of flow rates. Flow control 104 is coupled to luer lock 24, illustrated in FIG. 1, which in turn is in fluid communication with the interior lumen of the catheter, allowing delivery of Ringer's solution to the electrode 14 (FIG. 1). An electrosurgical generator 200 for providing R-F electrical energy is illustrated in functional block form, coupled to electrical connector 22 and to a ground plate electrode 202 (not drawn to scale).

While the embodiment illustrated above requires a second element (e.g. a guide catheter, guide wire or stylet) for advancing and positioning the catheter at its desired location, it is anticipated that the basic apparatus disclosed above may also be incorporated into catheters which themselves are steerable or deflectable, similar to R-F ablation catheters presently in clinical investigation. Similarly, it is anticipated that in commercial embodiments, alternative mechanisms (e.g. precision pumps) for controlling the flow of Ringer's solution may be employed. Similarly, while the inventors have employed Ringer's solution, other alternative fluids may be workable as well. As such, the embodiment discussed above should be considered exemplary, rather than limiting, in conjunction with the following claims.

In conjunction with the above specification, we claim:

1. A method of ablation comprising:

advancing a catheter, having a distal end carrying means extending distally therefrom for fixing said catheter to body tissue and an electrode extending at least two centimeters along an outer surface said catheter proximal to said distal end, to a desired location in a patient's body;

fixing said distal end of said catheter to body tissue using said fixing means;

after said fixing step, applying said electrode along a desired line of said body tissue; and thereafter ablating said body tissue along said desired line using said electrode.

2. A method according to claim 1 wherein said advancing step comprises advancing a catheter, having a tissue penetrating member extending distally from said distal end of said catheter and wherein said fixing step comprises advancing said penetrating member into said body tissue.

3. A method according to claim 2 wherein said advancing step comprises advancing a catheter having a helical tissue penetrating member.

4. A method according to claim 1 or claim 2 or claim 3 wherein said ablating step comprises applying R-F energy to said electrode.

5. A method of ablation, comprising:

advancing a catheter having a distal end and having a helical, tissue penetrating member extending from said distal end of said catheter and an elongated electrode, located proximal to said helical member and extending along a distal segment of an outer surface of said catheter, to a desired location in a patient's body;

fixing said distal end of said catheter to body tissue by rotating said helical member into body tissue;

after said fixing step applying said elongated electrode along said distal segment of said catheter to a desired line along said body tissue; and ablating said body tissue along said desired line using said electrode.

6. A method according to claim 5 wherein said ablating step comprises applying electrical energy to said electrode.

7. A method according to claim 6 wherein said ablating step comprises applying R-F energy to said electrode.

8. A method according to claim 5 or claim 7 wherein said advancing step comprises advancing a catheter having an elongated electrode extending at least two centimeters along said catheter.

9. A method according to claim 5 or claim 7 wherein said advancing step comprises advancing a catheter having an elongated coil electrode extending at least two centimeters along said catheter.

* * * * *